United States Patent [19]

Sneider

[11] Patent Number: 4,487,336
[45] Date of Patent: Dec. 11, 1984

[54] SYRINGE CLOSURE ASSEMBLY WITH ATTACHABLE NOZZLE

[76] Inventor: Vincent R. Sneider, 3422 Hallcrest Dr., Atlanta, Ga. 30319

[21] Appl. No.: 384,096

[22] Filed: Jun. 1, 1982

[51] Int. Cl.³ .............................................. A61M 1/00
[52] U.S. Cl. .................................. 222/107; 222/568; 222/570; 383/96; 604/132; 604/133
[58] Field of Search ................ 222/92, 107, 543, 545, 222/566, 567, 568, 570, 526; 604/131–133; 383/96; 220/85 SP

[56] References Cited

U.S. PATENT DOCUMENTS

| | | | |
|---|---|---|---|
| 3,235,147 | 2/1966 | Hamilton | 222/543 |
| 3,688,766 | 9/1972 | Kempel | 604/212 |
| 3,773,047 | 11/1973 | Sneider | 604/275 X |
| 3,892,311 | 7/1975 | Sneider | 604/197 X |
| 3,993,070 | 11/1976 | Sneider | 604/132 |
| 4,223,810 | 9/1980 | Sneider | 222/107 |

Primary Examiner—H. Grant Skaggs
Assistant Examiner—Lawrence J. Miller
Attorney, Agent, or Firm—Ralph R. Roberts

[57] ABSTRACT

This invention discloses a syringe closure used with a nozzle and flexible bag in which fluid is initially flowed. This closure apparatus includes a retainer ring of generally tubular and tapered construction. This retainer ring has an outwardly disposed groove formed at its lower and smaller diameter end in which a bead end of the flexible bag is mounted. An outer safety ring also of generally tubular configuration is mounted on this retainer ring and insures retention of the bead end of the bag in the groove. A nozzle retainer member having an inner aperture in which the nozzle is removably mounted has an outwardly generally circular projecting lip sized and adapted to snap in and seat in an inwardly disposed recess formed in the retainer ring. Where and when the nozzle retainer member is displaced from the arcuate retaining recess in the retainer ring the secured flexible bag may be manipulated to pass through the large aperture in the retainer ring and into an inside out condition whereat the inside surface of the bag may be washed and/or dried and then again manipulated through said large aperture to again be arrayed in the conventional position whereby it may be filled with fluid and the nozzle retainer member again mounted in the arcuate recess in the retainer ring.

7 Claims, 7 Drawing Figures

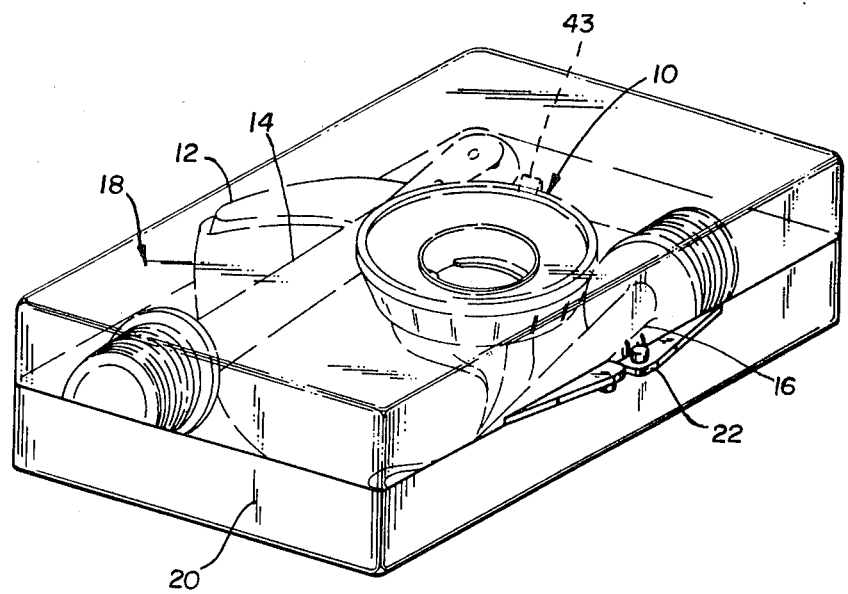
FIG. 1
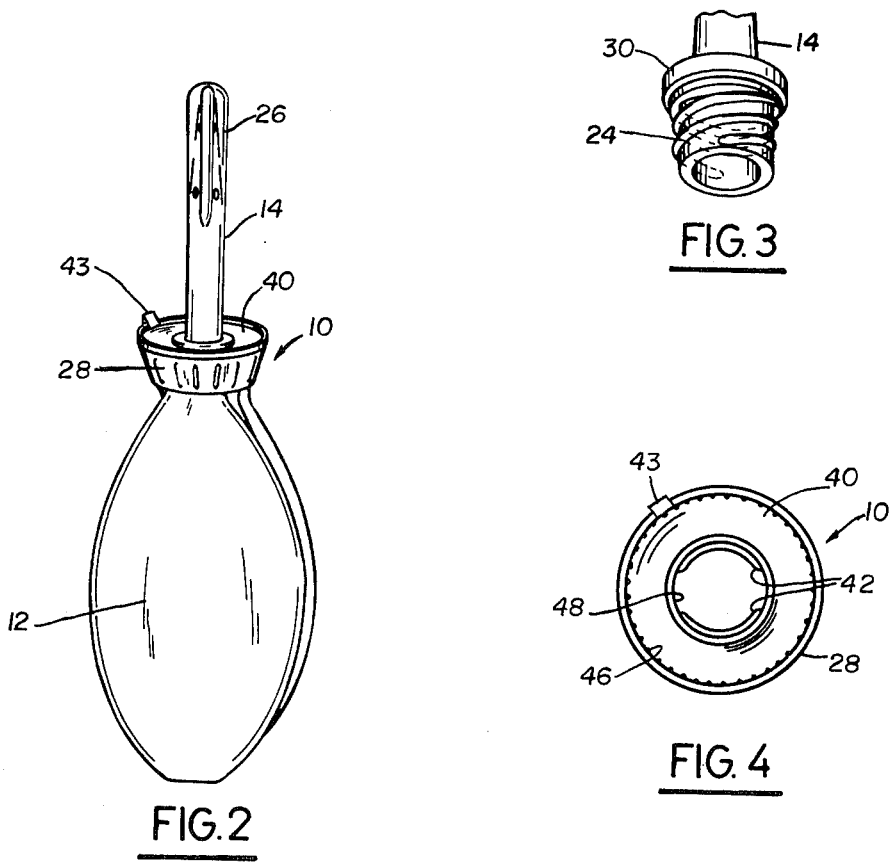
FIG. 3
FIG. 2
FIG. 4

SYRINGE CLOSURE ASSEMBLY WITH ATTACHABLE NOZZLE

BACKGROUND OF THE INVENTION

1. Field of the Invention

With relation to the field of art as established in and by the United States Patent Office this invention is believed to be found in the general class entitled, "Dispensing" (Class 222) and in the subclass therein entitled, "Collapsible Wall-Type Container-nonmetallic" (Subclass 107).

2. Description of the Prior Art

Feminine syringes with nozzle means are well known and are shown in several United States and foreign patents. Among these known syringes are Applicant's U.S. Pat. No. 4,233,810 as issued Sept. 23, 1980 and the references noted in this patent. These include U.S. Pat. No. 2,353,153 to FERREl; U.S. Pat. No. 2,644,893 to KEMPEL; U.S. Pat. No. 3,424,218 to VANDERBUR, Jr. et al., and U.S. Pat. No. 3,667,461 to ZAMARRA. Closures and means for closing said bags are also found in U.S. Pat. Nos. 3,144,866; 3,530,858; 3,589,362; 3,726,276; 3,773,047; 3,892,311 and 3,948,260.

In many instances the resiliency of the collapsible bag is relied upon for retention of the bag to the collar member. In this application as well as Applicant's U.S. Pat. No. 4,223,810 above noted the problem of a greater than normal force being applied to a collapsible bag does not cause dislodgement of said bag from the collar. The flexible bag utilizes the safety collar to retain the open end of the bag on the ring portion of the retainer so that dislodgement is prevented. The absence of a safety collar or retainer and a resultant excessive force may cause a dislodgement, at least in part, with a consequent spraying or spilling of the contents of the bag.

The present closure construction provides a novel closure and retainer for the flexible and elastic bag used therewith. The nozzle retainer is connected to the retainer ring by a small hinge-like portion that permits an inside out arrangement and then a washing of the flexible bag. This inside out exposure of the inside permits drying, and then reassembling in a conventional attitude for use withut loss of components. The retaining ring secures the flexible bag to the retainer ring in a positive manner while the nozzle can be removed or remounted in the threaded aperture as desired.

SUMMARY OF THE INVENTION

This invention may be summarized, at least in part, with reference to its objects. It is an object of this invention to provide, and it does provide, a nozzle retainer which is hingedly attached to a retainer ring which is partially resilient. This collar is positioned after a flexible bag is mounted on a ring portion formed on the retainer ring.

It is a further object of this invention to provide, and it does provide, a safety collar which is snapped into position to retain a flexible bag in a groove formed in a retainer ring. A nozzle retainer member having a threaded aperture for holding a flexible, attachable nozzle is hingedly attached to said retainer ring. Both the nozzle retainer and the retainer ring are made from the same plastic material which is partially resilient. This nozzle retainer is formed with a circular and protruding lip that is mountable in and provides a tight fit in a compatible recess formed in the retainer ring. In a seated condition the nozzle retainer and retainer ring provides the desired fluid seal when the syringe is used with fluid contained in the flexible bag. The aperture provided in the retainer ring when the nozzle retainer is removed from the recess or groove formed therein provides a larger aperture than conventionally is provided with screw mounted nozzles. The flexible bag in its mounted condition on the retainer ring may be pushed or manipulated through this larger central opening and brought to an inside out condition. In this condition the now outside surface (formerly interior surface) of the bag may be washed and/or dried. After the flexible bag has been dried or sufficiently cleaned so as to be reusable the flexible bag is pushed or manipulated through this opening in the retainer ring and is again brought to the usual condition. The safety collar is still in place to retain the bag which may now be filled with fluid and used or packed away in a travelling container.

In brief, this invention provides a retainer ring with a large central opening into which is frictionally seated a nozzle retainer generally circular and plate-like. The retainer ring and the nozzle retainer ring are of the same material and are molded at the same time with a hinge portion connecting these two members. When and as the nozzle retainer is displaced from the seated engagement in the groove in the retainer ring there is provided a generally circular opening or aperture through which the flexible bag may be passed for inside out cleaning and/or drying. The combination molding of the retainer ring and nozzle retainer is made of a plastic which has a slight resiliency and the nozzle retainer is formed with internal threads adapted to receive and retain the threaded end of a nozzle.

The flexible bag has an open end with a band or ring which is smaller than a retaining groove or lip provided on the retaining ring. This open end and band of the bag is snapped in position on this ring and then a safety retainer ring or collar is advanced to engage the retainer ring and is mounted in a securing position whereby the flexible bag is retained in this mounted condition and position. The hinged nozzle retainer and its internal threads removably retain a flexible or soft nozzle of conventional configuration. This nozzle retainer is snapped into a retaining position in an inwardly formed groove in the retainer ring and provides therewith a fluid seal.

In addition to the above summary the following disclosure is detailed to insure adequacy and aid in understanding of the invention. This disclosure, however, is not intended to cover each new inventive concept no matter how it may later be disguised by variations in form or additions of further improvements. For this reason there has been chosen a specific embodiment of a syringe closure as adopted for use with vaginal and rectal syringes and showing a preferred means for construction and use. This specific embodiment has been chosen for the purposes of illustration and description as shown in the accompanying drawings wherein:

BRIEF DESCRIPTION OF THE DRAWINGS

FIG. 1 is a perspective view illustrating and showing the syringe closure assembly of this invention including a hinged retainer ring and nozzle retainer and with a flexible bag mounted on said ring in a collapsed condition, one or more nozzles which may be mounted in the nozzle retainer are depicted in a travelling container which is closed and when in the encased condition provides a travelling kit;

FIG. 2 represents a perspective view of an assembled syringe in which the novel closure means is utilized;

FIG. 3 represents a partial and fragmentary perspective view of a threaded end of a flexible nozzle adapted for mounting and fluid tight retention in the nozzle retainer;

FIG. 4 represents a top or plan view of the closure assembly absent a nozzle and flexible bag;

In the following description and in the claims various details are identified by specific names for convenience. These names are intended to be generic in their application. Corresponding characters refer to like members throughout the seven figures of the drawings.

DESCRIPTION OF THE PREFERRED EMBODIMENT AS SEEN IN FIGS. 1 THROUGH 4

Figure 5:
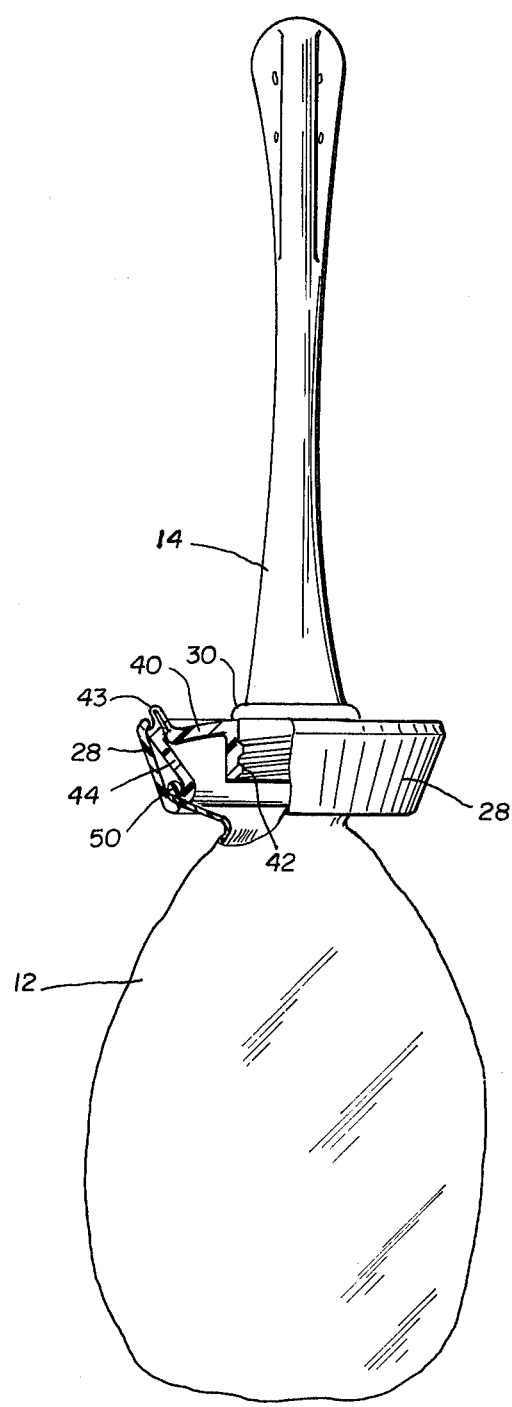
FIG. 5 represents a side or face view of the syringe assembly and with a central axis line showing a left half in a sectional view and with the right half depicting the outside appearance of the assembled syringe and mounted nozzle.

Referring now to the drawings and the embodiment shown therein, FIG. 1 shows a syringe that includes a closure means generally identified as 10. A bag 12 is of a fluid impervious material and is generally flexible. As seen in FIG. 1, this bag 12 and a feminine spray nozzle 14, or if desired a rectal nozzle 16, are packaged in a container or case 18 which is hinged to provide a travel kit 20. An an inexpensive kit the container may have a friction fit-type, snap open closure 22. Both nozzles 14 and 16 are conventional and have a screw thread 24 for removably mounting in a closure means 10.

FIG. 2 depicts the assembly of the syringe with the feminine spray nozzle 14 and shows a conventional head or distal portion 26 which has spray outlets and grooves well known in the art. Bag 12 is mounted on the closure means to be more fully described in relation to FIGS. 5, 6 and 7. An outer safety retainer ring 28 is also shown in this assembly view.

FIG. 3 depicts attaching means for the nozzle 14 or 16 in which the threads 24 are shown as a double helix-type for quick insertion, tightening and removal from the closure means. A stop shoulder 30 is provided on each nozzle to limit insertion and insure a seal of the nozzle in the closure means. Whether a feminine spray nozzle or a rectal nozzle is used the stem and end is usually of a flexible or soft material for the comfort of the user.

Figure 6:
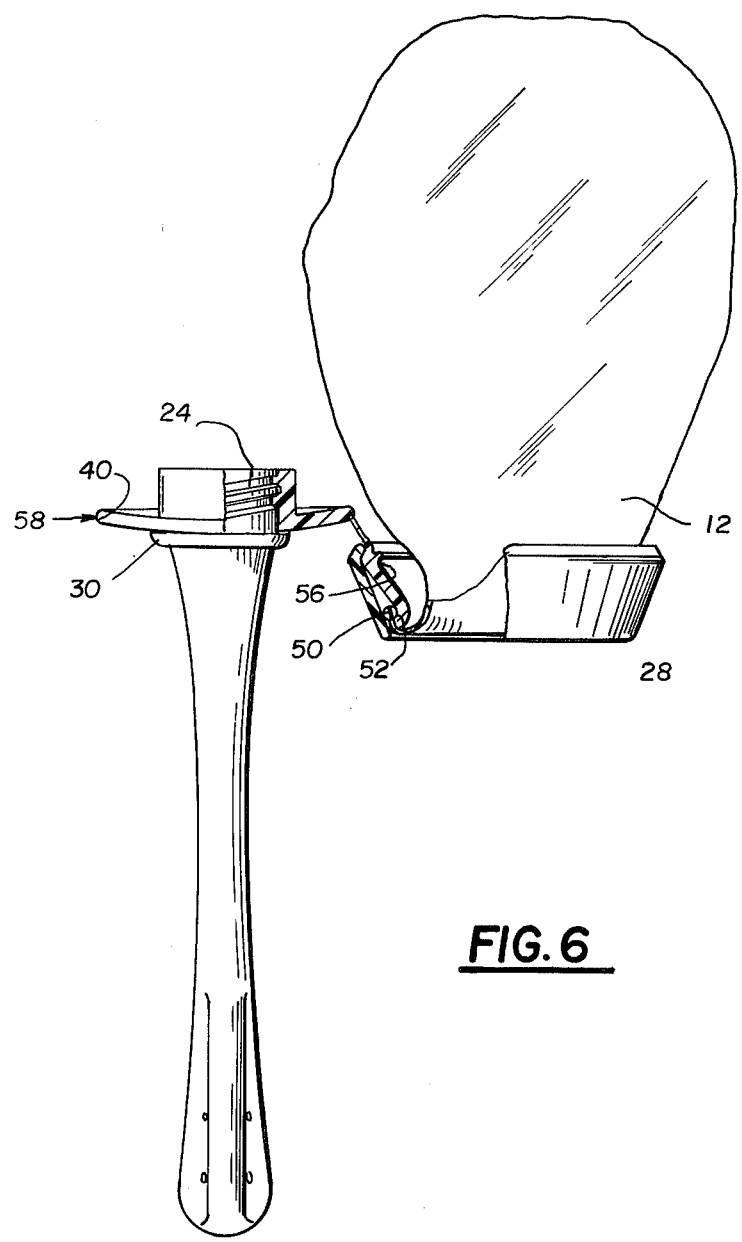
FIG. 6 represents a side or face view of the syringe assembly and with a central axis line showing, partly diagrammatically, the bag as mounted on a nozzle retainer and with said bag turned inside out for washing and/or drying and showing the nozzle retainer attached by an integral hinge portion.

FIG. 4 illustrates a top or plan view of the molded closure means 10 in which the outer safety ring 28 contains and retains a nozzle retainer member 40 having internal threads 42 to mate with and retain the threads 24 of the nozzle shown in FIGS. 1 and 3. Also depicted is a hinge portion 43 which extends from the nozzle retainer member 40 to a retainer ring 44 not seen in this view. Very shallow flutes or a knurl 46 may be formed on ring 44 and if so provided may be seen in this view. Such a configuration is shown in FIGS. 5 and 6 of Applicant's U.S. Pat. No. 4,223,810 above noted. An aperture 48 in retainer 40 contains threads 42.

EMBODIMENT AS SEEN IN FIGS. 5, 6 AND 7

Applicant's improved syringe closure contemplates that the bag 12 has an integral bead or band portion 50 adapted to be snapped on and in a circular groove portion 52 formed in retainer ring 44. This band portion 50 seats in groove portion 52 and an outwardly extending shoulder thereof provides the smooth lower retaining lip. This retainer ring is formed to extend upwardly and outwardly in a tapered configuration to a top rim whereat a small hinge portion 43 connects this retainer ring 44 to the nozzle retainer member 40. It is to be noted that the upper, inner portion of retainer ring 44 is formed with a circular retaining and arcuate recess 56 of a selected size and configuration.

The nozzle retainer member 40 is formed with an outwardly projecting lip 58 that is sized and disposed to snap into recess 56 provided in retainer ring 44. The inner through portion or aperture 48 of retainer member 40 has the female internal threads 42 in which is mounted a nozzle 14 or 16. Tightening of the nozzle in position insures that the mounting of the nozzle provides the fluid seal desired. The snap in action of projecting lip 58 in recess 56 also provides a fluid seal in the condition of FIG. 5.

USE AND OPERATION

The assembly contemplates that the bead or band 50 of bag 12 is stretched sufficiently for mounting in the groove 52 formed on retainer ring 44. After mounting this bag on the ring 44 the retainer ring 28 is advanced over the bag and is snapped in place with the upper and inturned lip portion engaging the upper outer circumferential diametrical portion of the retainer 44. The mounting of the bead 50 in the recess 52 and its retention is insured during use by the mounting of retainer ring 28 on the outer surface of ring 44. As noted in FIG. 6 the hinge portion 43 may extend over the upper rim of the retaining ring 44.

The hinged portion and inner nozzle retainer portion 40 is swung into place with the outward projecting lip 58 of retainer 40 being a tight retaining fit in arcuate recess 56 in ring 44. When assembled, the opening in the nozzle retaining member 40 is disposed to receive and retain the threaded end 24 of a nozzle. The stop shoulder 30 prevents and provides a limit to the inward rotational movement of the nozzle. Fluid with or without an additional medicament (often a powder with defined properties) is used with the flexible bag 12 and often the bag is squeezed to provide additional pressure.

After use it is often desirable to wash and/or dry the interior of the flexible bag. Prior to this invention this required elaborate disassembly procedures. The present invention as shown in FIG. 6 provides an easy manipulation for such a purpose. The nozzle retainer member 40 is displaced from the retainer ring 44 by causing the outwardly projecting lip 58 to be displaced from the circular retaining recess 56. The flexible nozzle 14 or 16 may be used as a pry assist to move retainer member 40 from the retaining arcuate recess 56. Hinge 43 allows the swinging of the nozzle and nozzle retainer member 40 to the position of FIG. 6 after which the bag 12 is turned inside out by passing the bag through the central opening in the retainer ring 44.

After drying the bag 12, reassembly is relatively easy. Bag 12 is manipulated through the large central opening in retainer ring 44 and while secured is either collapsed for storage in the travel kit 20 or is filled with fluid and when and where desired with added components. The nozzle retainer member 40 is again swung or snapped into place to provide a fluid tight seal of the outwardly projecting lip 58 in the arcuate recess 56 in retainer ring 44.

Figure 7:
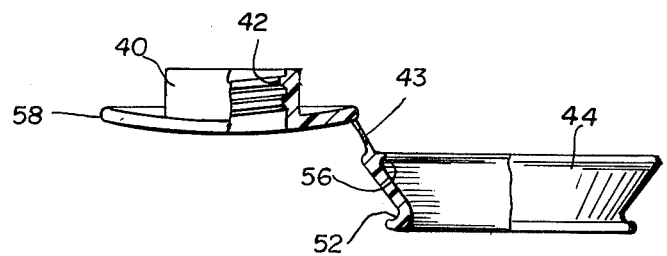
FIG. 7 represents a sectional side view of the molded and hingedly attached nozzle retainer and the bag retainer ring in an as-molded condition.

It is to be noted that the showing in FIGS. 5, 6 and 7 is substantially full size and the central opening as seen in the retainer ring 44 is about one and three-eighths inches in diameter. Through this opening the flexible bag 12, although secured at its top or open end by band 50 is easily manipulated to provide the inside out condition of FIG. 6. After washing and/or drying the flexible bag is once again manipulated through this aperture or opening and into the arrangement of FIG. 2 whereby fluid may be flowed into the bag through said opening in the retainer ring.

It is to be noted that the flexible nozzle is usually molded of a soft material which may or may not be plastic. These flexible nozzles have a generally central conduit for the carrying of fluid from the bag to the outlet or outlets at or near the tip of the nozzle. The outwardly extending lip 58 of the nozzle retainer 40 is a friction fit with the circular recess or groove 56 in the retainer 44.

It is to be noted that container 20 is usually of inexpensive plastic with an integral hinge portion. The syringe assembly of FIG. 2 may be absent of the container 20 which is merely a suggested kit retainer. The nozzle 14 or 16 is conventional and rather than threads 24 as in FIG. 3 the nozzle may be mounted as a snap-in member or by other securing means. The molding of member 40 has its central aperture 48 for the nozzle formed to suit. The hinge 43 is usually provided since it reduces the probability of separation and loss but this does not preclude the making of the nozzle retainer 40 and the retainer ring 44 as separate components absent an integral hinge 43.

Bag 12 is usually of very flexible material such as plastic but the use of a coated material is also contemplated particularly where additional powders used with the fluid are contemplated. What is important is that the bag 12 have a resilient and stretchable bead or band 50 which snugly seats in the groove 52 formed in the retainer ring 44. The retainer member 28 insures that the mounted bag 12 is not dislodged from the recess or groove 52 in the retaining ring 44. Safety retainer 28 is mounted on retainer 44 and as shown in FIG. 5 engages the bottom of retainer ring 44 and snaps in place over the upper lip or shoulder also provided on retainer ring 44.

A fluted upper rim of the retaining ring is depicted at FIGS. 5 and 6 of Applicant's U.S. Pat. No. 4,223,810 above referenced. This same fluted design may be employed on the retaining ring 44 of the present invention and is suggested or indicated in the drawing of this application at FIG. 4. The hinge 43 is depicted as having an upward cant or disposition with this angle provided so that the hinge does not unduly engage the safety retainer ring 28 when mounted on the retainer ring 44. This hinge is made so that when the nozzle retainer 40 is swung to the condition and position of FIG. 6 said hinge does not unduly engage the upper portion of the safety retainer ring 28.

It is to be noted that the retaining ring provided in Applicant's above identified U.S. Pat. No. 4,223,810 is solid and does not show or suggest a nozzle retainer member 40 that is plate-like in configuration. When swung to the position of FIG. 6 a large through aperture or opening in retainer ring 44 is provided. This large opening which is believed to be novel allows the flexible bag to be moved to and through the opening. This manipulation of the flexible bag 12 does not disturb the retention of the bag by band 50 in the groove 52 insured by the safety ring or collar 28. It is to be noted that the hinge 43 is contemplated to be an integral member formed with members 40 and 44 when molded but this does not preclude forming the hinge and securing this hinge as a separate member. It is to be further noted that the outer safety ring 28 has a generally tapered configuration that allows only one way mounting on the retainer ring 44. As seen in FIGS. 5 and 6 this construction insures ready and rapid assembly and provides positive retention of bead 50 in groove 52. Ring 28 may or may not be of partially resilient material.

The drawings depict the retainer ring 44 as of a generally tubular configuration and with a taper leading from a smaller bottom end to a larger upper or top end. This is the preferred molding configuration but this is not to preclude the forming of this ring in configurations other than shown. The outer safety ring 28 is shown as engaging both the upper and lower ends of the retainer ring 44 but this is not to preclude an engaging means formed intermediate the ends as long as flexible bag 12 and its bead or band 50 is retained in groove 52. As the outwardly projecting lip 58 snaps into the recess 56 in retainer ring 44 at least one of the members 40 or 44 is made partially resilient for a snap-in retention.

Terms such as "left", "right", "up", "down", "bottom", "top", "front", "back", "in", "out" and the like are applicable to the embodiment shown and described in conjunction with the drawings. These terms are merely for the purposes of description and do not necessarily apply to the position in which the syringe closure with snap-in nozzle retainer may be constructed or used.

While a particular embodiment of the closure apparatus has been shown and described it is to be understood the invention is not limited thereto and protection is sought to the broadest extent the prior art allows.

What is claimed is:

1. A syringe closure assembly with retaining means for an attachable nozzle, the nozzle having sufficient resiliency for comfort by the user and having a fluid passageway therein and compatible attaching means to the closure assembly, said closure assembly including:
   (a) a retainer ring of a generally tubular configuration and having an aperture therethrough and a lower end of said ring having an outwardly directed annular groove portion formed thereon and at the other end of said retainer ring there is formed an inwardly disposed annular arcuate retaining recess;
   (b) a nozzle retainer member having an inner aperture formed to provide detachable mounting and retaining means for a syringe nozzle, said nozzle retainer having an outwardly generally circular and planar projecting lip sized and adapted to snap into and thereby seat in a fluid tight manner with the inwardly disposed arcuate retaining recess in the retainer ring;
   (c) a hinge connection having one end attached to an edge portion of the retainer ring and the other end attached to an outer extreme portion of the nozzle retainer, said hinge being of molding material that is slightly resilient and being integral with the retainer ring and nozzle retainer member so that substantially simultaneous molding may be performed, said hinge canted upwardly so as to avoid obstruction to inserting and seating the projecting lip of the nozzle retainer in the inwardly disposed arcuate retaining recess in the retainer ring when said projecting lip and said retaining recess are attachably mounted;

(d) a flexible bag of material generally impervious to fluid contained therein and having a resilient neck portion which includes a bead or band which is mountable in the outwardly directed annular groove portion of the retainer ring; and (e) an outer safety retainer ring of a generally tubular configuration and having at least one retaining means formed thereon and disposed to engage and to be secured onto the retainer ring by engagement with the outer surface of said retainer ring thereby to retain the mounted bead or band of said flexible bag in said groove of the retainer ring, whereby when the nozzle retainer member is displaced from the arcuate retaining recess in the retainer ring, the secured flexible bag may be manipulated pass through the aperture in the retainer ring and into an inside-out condition whereby the inside surfaces of the bag may be washed and/or dried and then again manipulated through said aperture to be arrayed in a conventional position whereby it may be filled with fluid and the nozzle retainer membe snapped into place to provide mounted retention in the arcuate recess in the retainer ring.

2. A syringe closure assembly as in claim 1 in which the nozzle retainer member has a generally flat configuration with the projecting lip formed as an outer extreme portion of said member.

3. A syringe closure assembly as in claim 1 in which the nozzle is made of a soft material and the retaining means are male threads formed on the mounting end of the nozzle and said male threads are attachably secured to compatible female threads formed in the inner aperture of the nozzle retainer member.

4. A syringe closure assembly as in claim 3 in which the nozzle is provided with an outwardly extending flange providing a limiting stop shoulder and seal for fluid flow from the bag and through the nozzle.

5. A syringe closure assembly as in claim 1 in which the retainer ring is formed with a taper, said lower end having a lesser diameter and the other end having a larger diameter.

6. A syringe closure assembly as in claim 5 in which the outwardly directed groove portion and inwardly disposed arcuate recess are each made with their cross sectional configurations as portions of a circle.

7. A syringe closure assembly as in claim 5 in which the outer safety retainer ring is also of a tapered tubular configuration and with the upper and lower ends thereof having inwardly disposed lip portions adapted to engage and to be retained on the outer engaging diameters of the retainer ring with at least a portion of said flexible bag disposed between said lower lip portion and its corresponding engaging diameter.

* * * * *